United States Patent [19]

Suzuki et al.

[11] Patent Number: 5,344,586
[45] Date of Patent: Sep. 6, 1994

[54] ANTIFERROELECTRIC LIQUID CRYSTAL COMPOUND AND PROCESS FOR PRODUCING THE SAME

[75] Inventors: Yoshiichi Suzuki; Hiroyuki Mogamiya, both of Tokyo; Koichi Tanaka; Yoshihiro Takagi, both of Kobe; Katutoshi Hirose, Kobe, all of Japan

[73] Assignee: Showa Sheel Sekiyu Kabushiki Kaisha, Tokyo, Japan

[21] Appl. No.: 63,687

[22] Filed: May 20, 1993

[30] Foreign Application Priority Data

May 21, 1992 [JP] Japan .................. 4-154388

[51] Int. Cl.$^5$ .................. C09K 19/20; C09K 19/12; C07C 323/62; C07C 327/32
[52] U.S. Cl. .................. 252/299.64; 252/299.62; 252/299.65; 252/299.66; 252/299.67; 560/4; 560/17
[58] Field of Search .................. 252/299.01, 299.62, 252/299.64, 299.65, 299.66, 299.67; 560/9, 17, 87, 102, 147, 152

[56] References Cited

U.S. PATENT DOCUMENTS 5,207,947 5/1993 Suzuki et al. .................. 252/299.67

FOREIGN PATENT DOCUMENTS 0390759 10/1990 European Pat. Off. .
0422996 4/1991 European Pat. Off. .
63-222147 9/1988 Japan .
344367 2/1991 Japan .

OTHER PUBLICATIONS

N. H. Trinh et al., "Chiral SC* Phase in Some Thiobenzoates Series*", Molecular Crystals and Liquid Crystals, Letters Section, vol. 4, No. 3-4, 1987, pp. 93-98.

Primary Examiner—Robert L. Stoll
Assistant Examiner—Shean C. Wu
Attorney, Agent, or Firm—Cushman, Darby & Cushman

[57] ABSTRACT

A novel antiferroelectric liquid crystal compound is disclosed which is represented by the following formula:

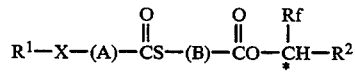

wherein $R^1$ and $R^2$ are independently selected from $C_3$-$C_{18}$ alkyl groups, respectively, Rf is a lower fluoroalkyl group, X is a group selected from the group consisting of —O—, —COO—, —OCO—, and —CO—, or a single bond, (A) and (B) each is a group independently selected from the group consisting of phenyl, biphenyl, and naphthalene group which may be substituted with a halogen atom, and C having an asterisk indicates an asymmetric carbon atom. A process for producing the antiferroelectric liquid crystal compound is also disclosed.

10 Claims, 3 Drawing Sheets

APPLIED TRIANGULAR WAVE VOLTAGE

OPTICAL RESPONSE OF NEMATIC LIQUID CRYSTAL ON MARKET

OPTICAL RESPONSE OF LIQUID CRYSTAL HAVING IDEAL BISTABLE STATES

OPTICAL RESPONSE OF LIQUID CRYSTAL HAVING TRISTABLE STATES OF PRESENT INVENTION

[−V] APPLIED VOLTAGE

[+V] APPLIED VOLTAGE

LIQUID CRYSTAL LAYER

[−V] APPLIED VOLTAGE

[0V]

[+V] APPLIED VOLTAGE

LIQUID CRYSTAL LAYER

ANTIFERROELECTRIC LIQUID CRYSTAL COMPOUND AND PROCESS FOR PRODUCING THE SAME

FIELD OF THE INVENTION

The present invention relates to a novel liquid crystal compound having a thioester linkage (—COS—).

Most of the optically active liquid crystal compound of the present invention has a ferroelectric property showing bistable states and, also, has an antiferroelectric property showing optically tristable states. The liquid crystal compound is used for display elements and electrooptical devices utilizing the response to the changes in an electric field.

BACKGROUND OF THE INVENTION

As electrooptical apparatuses using a liquid crystal, electrooptical apparatuses using nematic liquid crystals such as a DSM type display, TN type display, G-H type display, or STN type display have been developed and practically used. However, all of the electrooptical apparatuses using such nematic liquid crystals suffer the drawback response time is as slow as several milli sec to several tens milli sec, which results in a limited range of applications. The slow response of the electrooptical apparatuses or elements using nematic liquid crystals is due to the fact that the torque which changes the direction of molecules is inherently based on the anisotropy of dielectric constant and thus, the force is not so strong. With such a technical background, the development of a ferroelectric liquid crystal had been attempted which has a spontaneous polarization (Ps), has a strong torque based on Ps×E (E is an applied voltage), and has an extremely short optical response time of few $\mu$sec to several tens $\mu$sec to make the preparation of a ultrahigh speed device possible.

Mayer et al. synthesized DOBAMBC (p-decyloxybenzilidene-p-ammino-2-methylbutyl cinnamate) in 1975 for the first time in the world and which was confirmed to be a ferroelectric liquid crystal (Le Journal de Physique, Vol. 36, 1975, L-69).

Further, since Clark and Lagerwall reported in 1980 on such characteristics on display devices as high velocity response of submicroseconds and memory characteristics of DOBAMBC, ferroelectric liquid crystals have drawn considerable public attention (N. A. Clark et al., Appl. Phys. Lett. 36, 899 (1980)).

However, many technical problems in the above mentioned system have presented obstacles to its practical application. In particular, no material was reported as exhibiting ferroelectric liquid crystallinity at an ambient temperature. Moreover, an effective and practical method was not established to control the molecular alignment of the liquid crystal molecules. Control of the molecular alignment is essential in order to have an effective and practical liquid crystal display device.

After the publication of the report, various attempts have been made from both aspects of liquid crystal materials and device, display devices utilizing the switching between twisted bistable states were prepared for trial, and high speed electrooptical apparatuses using the device are proposed in U.S. Pat. No. 4,367,924 and others. However, high contrast and proper potential of threshold value have not been obtained.

From such a point of view, other switching systems were explored to propose a transitional diffusion system. Subsequently, a three states switching system of liquid crystal having tristable states was reported in 1988 (A. D. L. Chandani, T. Hagiwara, Yo Suzuki et al., Japan, J. of Appl. Phys., 27, (5), L729–L732 (1988)).

The optically tristable states herein referred to mean that, when voltage in the form of a triangular wave as in FIG. 1 A is applied to liquid crystal electrooptical devices where antiferroelectric liquid crystals are laid between the first electrode substrate plate and the second electrode substrate plate which is apart at a given space from the first one, the antiferroelectric liquid crystal shows the first stable molecular orientation and resulting the first optically stable state shown in FIG. 3 (a), and FIG. 1 (D) at point 2, respectively, when electric voltage is zero. The antiferroelectric liquid crystal shows the second stable molecular orientation and resulting the second optically stable state shown in FIG. 3 (b), and FIG. 1 (D) at point 1, respectively, in one of the direction of electric field and shows the third stable molecular orientation and resulting the third optically stable state shown in FIG. 3 (c), and FIG. 1 (D) at point 3, respectively, in the other direction of electric field.

Liquid crystal electrooptical apparatuses utilizing the tristable states, that is three states, are proposed in U.S. Pat. No. 5,046,823 filed by the present applicant.

The characteristics of an antiferroelectric liquid crystal showing the tristable states are described in more detail below.

In the ferroelectric liquid crystal element having a stabilized surface which was proposed by Clark-Lagawall, ferroelectric liquid crystal molecules show two stable states in which the molecules are uniformly oriented or aligned in one direction in the phase S*C. The molecules are stabilized in either state depending on the direction of applied electric field as shown in FIG. 2 at point (a) and at point (b), and the state is kept even when the electric field was shut off.

Actually, however, the alignment of the ferroelectric liquid crystal molecules shows twisted two states in which directors of the liquid crystal molecules are twisted or shows a chevron structure in which layers are bent in a doglegged shape. In the chevron layer structure, switching angle becomes small, forming a cause for a low contrast, and which constitute a serious obstacle for its practical use.

On the other hand, in the liquid crystal electrooptical devices, an "anti" ferroelectric liquid crystal molecules are aligned in antiparallel, tilting in opposite direction at every adjoining layer, in the phase S*$_{(3)}$ showing the tristable states, and thus, the dipoles of the liquid crystal molecules are negating each other. Accordingly, the spontaneous polarization is nullified as a whole. The transmittance of the liquid crystal phase showing such molecular alignment corresponds to point 2 in FIG. 1 D.

Further, when a voltage sufficiently higher than a threshold value of (+) or (−) was applied, liquid crystal molecules shown in FIG. 3 (b) or (c) are tilted in the same direction and aligned in parallel. In this state, the spontaneous polarization is produced since the dipoles are also shifted to the same direction to form a ferroelectric phase, and the transmittance of the liquid crystal phase in that state corresponds to points 1 and 3 in FIG. 1 D.

That is, in the phase S*$_{(3)}$ of the "anti" ferroelectric phase, the "anti" ferroelectric phase at the time of no-electric field and two ferroelectric phases due to the polarity of applied electric field are stabilized, and switching is carried out among tristable states of an "anti" ferroelectric phase and two ferroelectric phases, with a direct current-like threshold value. Based on the change in the alignment of liquid crystal molecules accompanied with the switching, light transmittance is changed while drawing such a double hysteresis as shown in FIG. 4.

One of the characteristics of the present invention is that a memory effect can be realized by applying a bias voltage to the double hysteresis as shown in FIG. 4 (A) and then, further applying a pulse voltage.

Moreover, the ferroelectric phase is stretched in terms of its layer by the application of an electric field to form a book-shelf structure. On the other hand, in the "anti" ferroelectric phase of the third stable state, an analogous book-shelf structure is formed. Since the layer structure switching due to the application of an electric field gives a dynamic shear to liquid crystal layers, an alignment defect is improved during driving, and thus, a good molecular alignment can be realized.

In the "anti" ferroelectric liquid crystal, since image display is performed by alternatively using both hysteresises of plus side and minus side, afterimage phenomenon due to the accumulation of inner electric field based on the spontaneous polarization can be prevented.

As explained above, the "anti" ferroelectric liquid crystal can be said to be a very useful liquid crystal compound having advantages as follows:

1) Ultrahigh speed response is possible,
2) High contrast and wide viewing angle can be expected, and
3) Excellent alignment characteristics and memory effect can be realized.

Reports are made on the liquid crystal phase of the "anti" ferroelectric liquid crystal showing the tristable states in the following articles:

1) A. D. L. Chandani et al., Japan J. Appl. Phys., 28, L-1265 (1989), and
2) H. Orihara et al., Japan J. Appl. Phys., 29, L-333 (1990).

The liquid phase is called "Phase $S^*_{CA}$" (Antiferroelectric Smectic C phase) in association with the "anti" ferroelectric property. The phase is named "phase $S^*_{(3)}$" in the present specification since the liquid crystal phase performs the switching among tristable states.

The liquid crystal compounds which have the "anti" ferroelectric phase $S^*_{(3)}$ showing the tristable states in a phase series are disclosed in Japanese Unexamined Patent Publication No. 1-316367, U.S. Pat. Nos. 5,171,471 and 4,973,738, and European Patent No. 330,491 A filed by the present inventors, and in Japanese Unexamined Patent Publication No. 1-213390 filed by Ichihashi et al. Liquid crystal electrooptical devices utilizing the tristable states are proposed in Japanese Unexamined Patent Publication No. 2-40625 and U.S. Pat. No. 5,046,823.

The liquid crystal compounds having a thioester linkage are reported in Japanese Unexamined Patent Publication Nos. 63-222147 and 3-44367, and U.S. Pat. No. 5,068,054.

However, in Japanese Unexamined Patent Publication No. 63-222147, optically active alcohols such as 2-methyl pentanol are used while the liquid crystal phase shows a ferroelectric peoperty.

Besides, the liquid crystal compound in Japanese Unexamined Patent Publication No. 3-44367 has a thioester linkage in a side chain of its molecular structure and does not show a ferroelectric property, being different from the compound of the present invention.

Further, in U.S. Pat. No. 5,068,054, optically active alcohols such as 2-alkanol are used while the liquid crystal compound has a thioester skelton and shows a ferroelectric property.

As will be understood from the above, publications have disclosed neither a chemical structure in which a fluoroalkyl group is bonded to an asymmetric carbon atom nor such a ferroelectric liquid crystal phase $S^*_{(3)}$ as the compound of the present invention.

SUMMARY AND OBJECTS OF THE INVENTION

An object of the present invention is to provide a novel antiferroelectric liquid crystal compound. The novel antiferroelectric liquid crystal compound of the present invention is representable by the following formula:

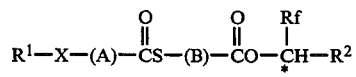

wherein $R^1$ and $R^2$ are independently selected from $C_3$ to $C_{18}$ alkyl groups, respectively, Rf is a lower fluoroalkyl group, X is a group selected from the group consisting of —O—, —COO—, —OCO—, and —CO—, or a single bond, (A) and (B) each is a group independently selected from the group consisting of 1,4-phenylene, biphenylene, and naphthalene which may be substituted with a halogen atom, and the C having an asterisk indicates an asymmetric carbon atom. A process for producing the novel antiferroelectric liquid crystal compounds is also disclosed.

BRIEF DESCRIPTION OF THE FIGURES

FIG. 1 (B), FIG. 1 (C) and FIG. 1 (D) show optical response characteristics of a commercially available nematic liquid crystal, of a liquid crystal exhibiting bistable states, and of a liquid crystal showing tristable states, respectively.

DETAILED DESCRIPTION OF THE INVENTION

Figure 1A:
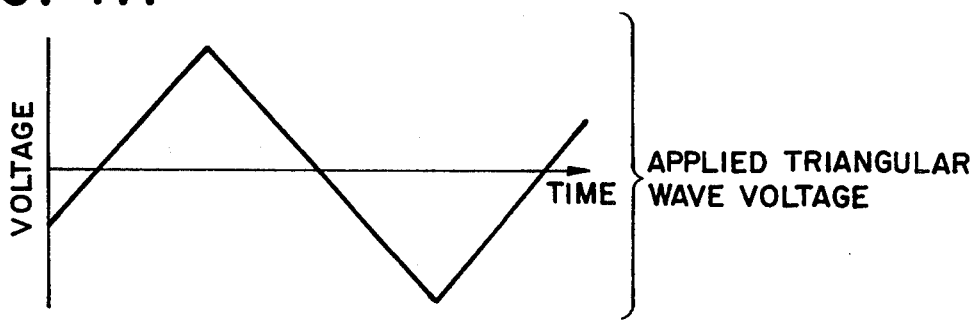
FIG. 1 (A) shows an applied triangular wave.
Figure 1B:
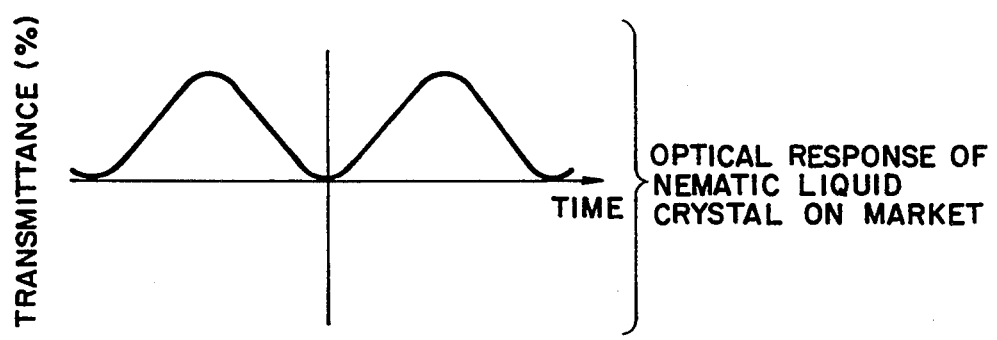
Figure 1C:
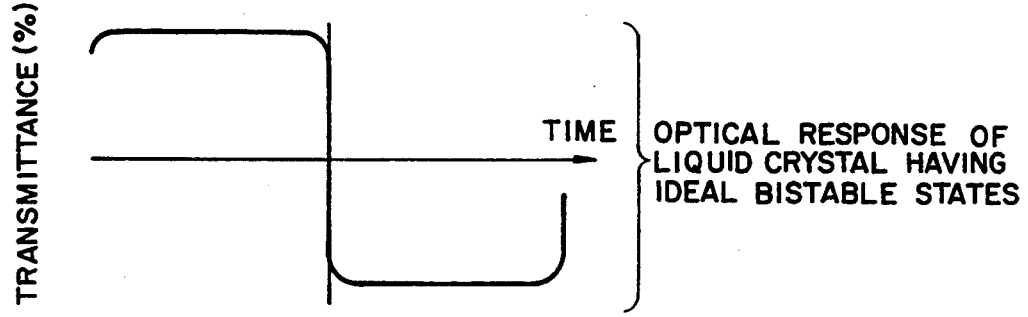
Figure 1D:
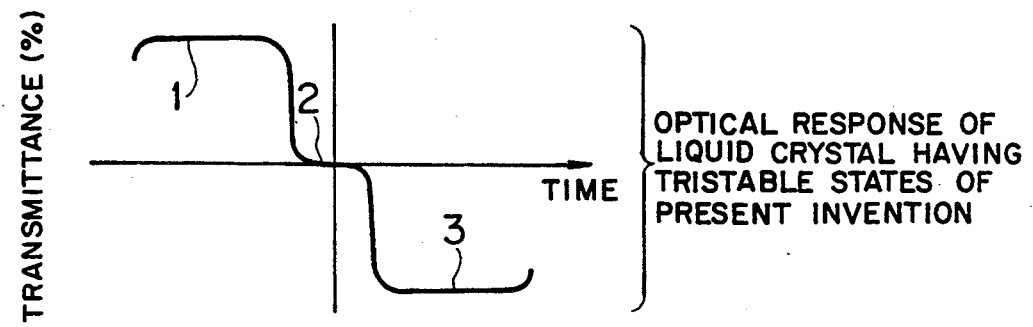
Figure 2A:
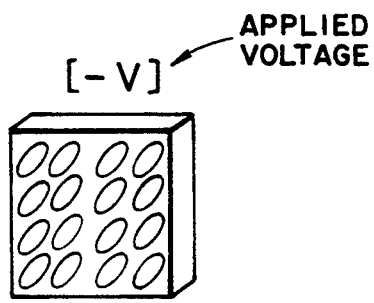
FIG. 2 shows the appearance of aligned ferroelectric liquid crystal molecules in two stabilized states, designated by rerference letters (a) and (b), as proposed by Clark and Lagerwall.
Figure 2B:
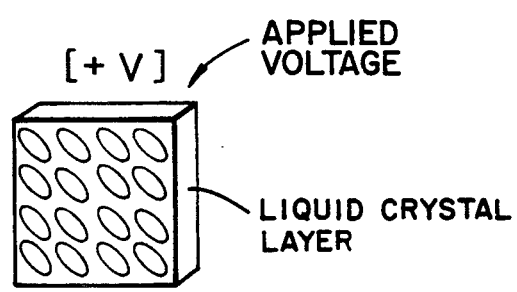
Figure 3A:
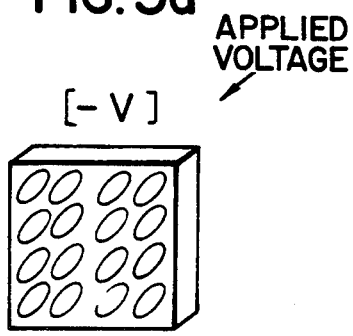
FIG. 3 shows the appearance of aligned "anti" ferroelectric liquid crystal molecules of the present invention in three different stable states, which states are designated by the reference letters (a), (b) and (c).
Figure 3B:
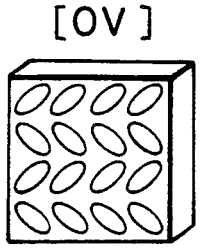
Figure 3C:
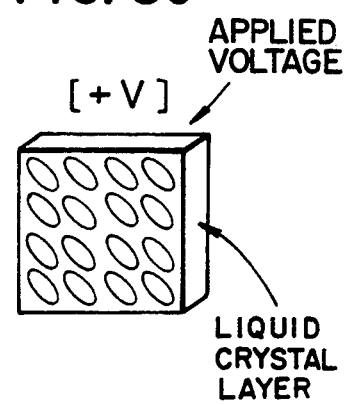
Figure 4:
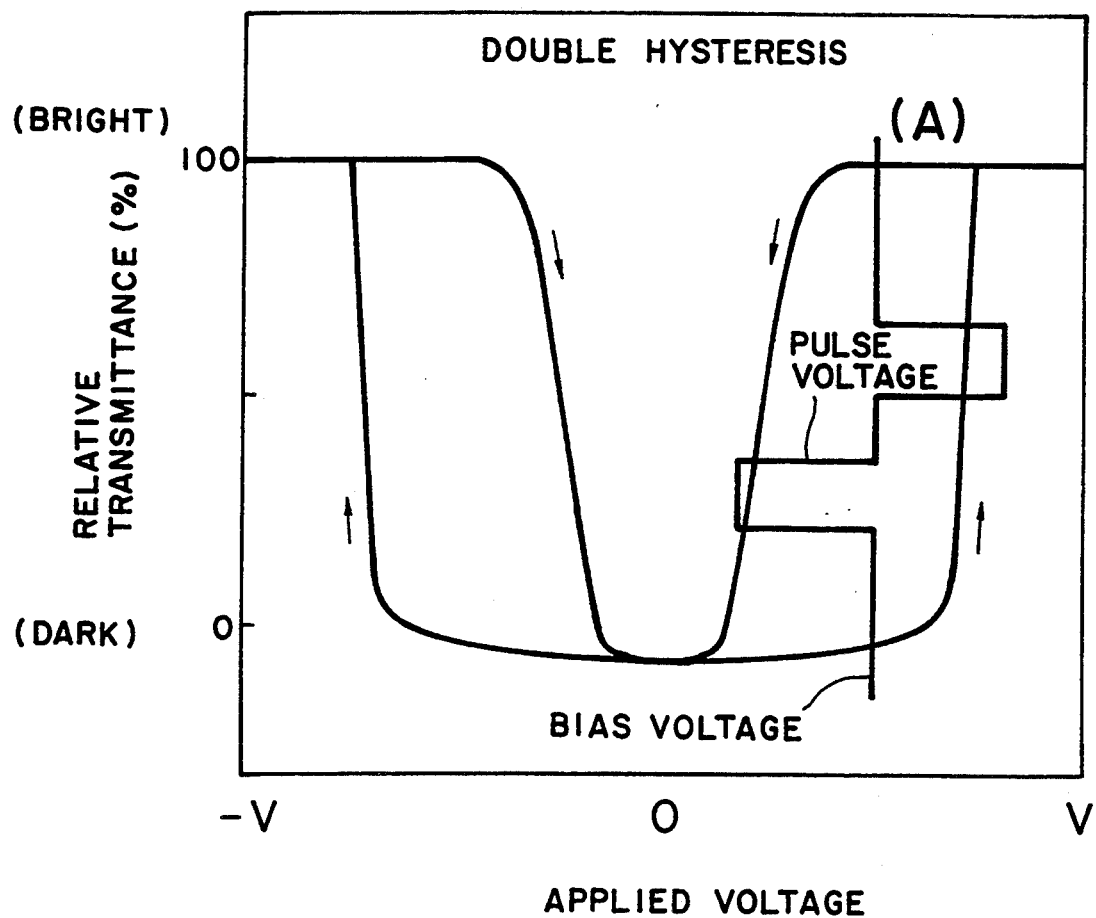
FIG. 4 is a graph showing characteristics of applied voltage-light transmittance indicating that antiferroelectric liquid crystal molecules change their light transmittance while drawing double hysteresis curves following the applied voltage. Reference point (A) in FIG. 4 refers to application of a bias voltage to the double hysteresis and further applying a pulse voltage.

The present invention relates to an antiferroelectric liquid crystal compound represented by the following formula:

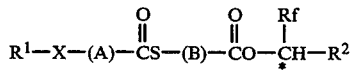

wherein $R^1$ and $R^2$ are independently selected from $C_3$–$C_{18}$ alkyl groups, respectively, Rf is a lower fluoroalkyl group, X is a group selected from the group consisting of —O—, —COO—, —OCO—, and —CO—, or a single bond, each of the (A) and (B) is a group independently selected from the group consisting of phenyl, biphenyl, and naphthalene group which may be substituted with a halogen atom, and C having an asterisk indicates an asymmetric carbon atom.

It is preferable in the present invention that the (A) in the general formula mentioned above is a group selected from the group consisting of

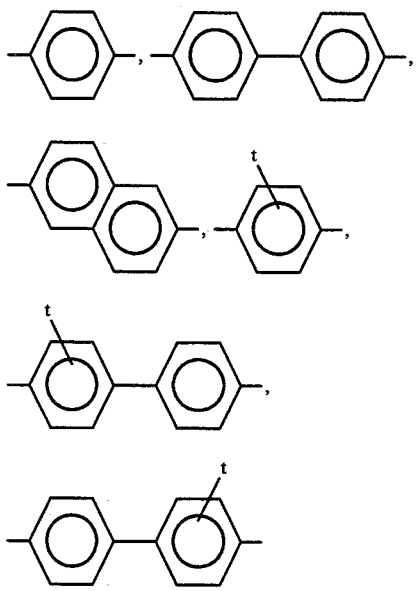

and the (B) in the general formula mentioned above is a group selected from the group consisting of

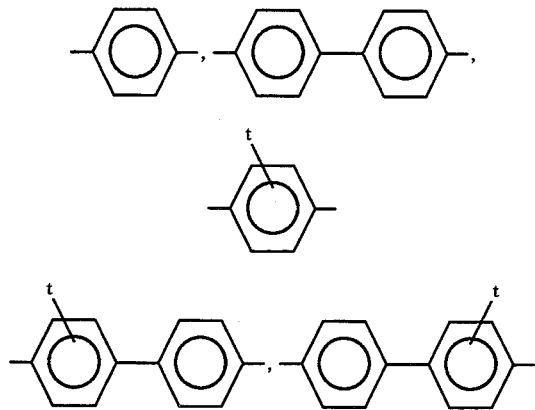

wherein t represents a halogen atom and Rf is a group selected from the group consisting of $CF_3$, $C_2F_5$, $CHF_2$ and $CH_2F$.

Besides, it is more preferable in the present invention that the (A) is

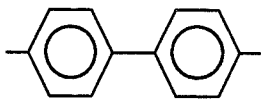

group and (B) is

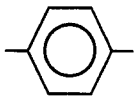

group.

Further, the present invention relates to a process for producing an antiferroelectric liquid crystal compound comprising subjecting an acid halide represented by the following formula:

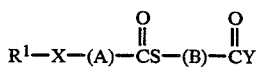

wherein $R^1$, X, (A), and (B) are the same as those mentioned above, and Y represents a halogen atom, to an esterification with an optically active haloalkyl-2-alkanlol represented by the following formula:

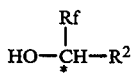

wherein $R^2$ is the same as mentioned above and Rf is a group selected from the group consisting of $CF_3$, $C_2F_5$, $CHF_2$ and $CH_2F$.

Still further, the present invention relates to a process for producing an antiferroelectric liquid crystal compound comprising subjecting a disulfide diacid chloride represented by the following formula:

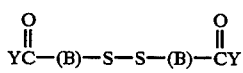

wherein (B) is the same as mentioned above and Y represents a halogen atom, to esterification with an optically active haloalkyl-2-alkanol or haloalkyl-3-alkanol represented by the following formula:

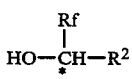

wherein $R^2$ and Rf are the same as mentioned above, to obtain an ester represented by the following formula:

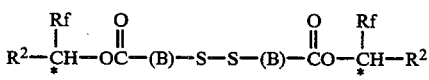

and then reacting the ester with a carboxylic acid represented by the following formula: $R^1$—X—(A)—COOH wherein $R^1$, X and (A) are the same as mentioned above.

The compound of the present invention can be produced by the method as follows:

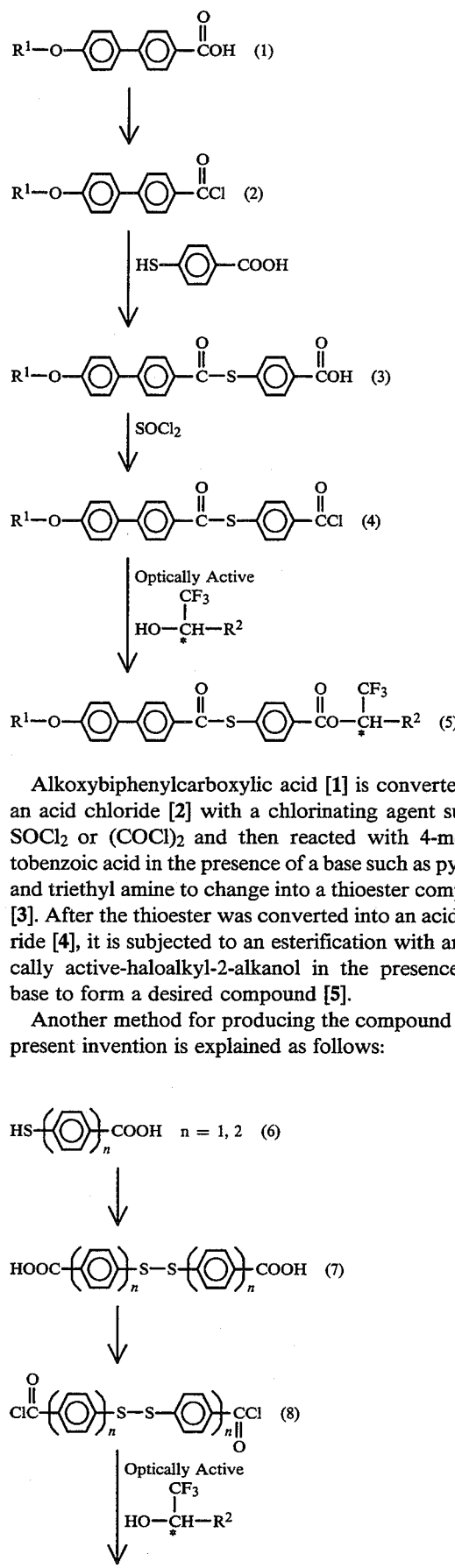

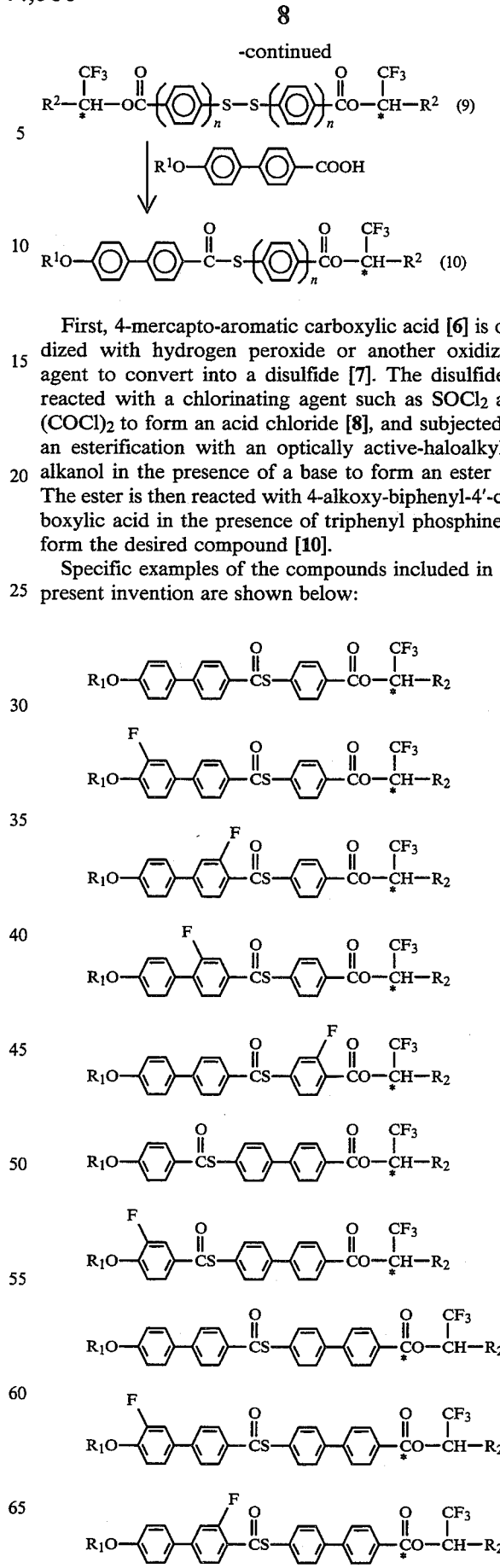

Alkoxybiphenylcarboxylic acid [1] is converted into an acid chloride [2] with a chlorinating agent such as $SOCl_2$ or $(COCl)_2$ and then reacted with 4-mercaptobenzoic acid in the presence of a base such as pyridine and triethyl amine to change into a thioester compound [3]. After the thioester was converted into an acid chloride [4], it is subjected to an esterification with an optically active-haloalkyl-2-alkanol in the presence of a base to form a desired compound [5].

Another method for producing the compound of the present invention is explained as follows:

First, 4-mercapto-aromatic carboxylic acid [6] is oxidized with hydrogen peroxide or another oxidizing agent to convert into a disulfide [7]. The disulfide is reacted with a chlorinating agent such as $SOCl_2$ and $(COCl)_2$ to form an acid chloride [8], and subjected to an esterification with an optically active-haloalkyl-2-alkanol in the presence of a base to form an ester [9]. The ester is then reacted with 4-alkoxy-biphenyl-4'-carboxylic acid in the presence of triphenyl phosphine to form the desired compound [10].

Specific examples of the compounds included in the present invention are shown below:

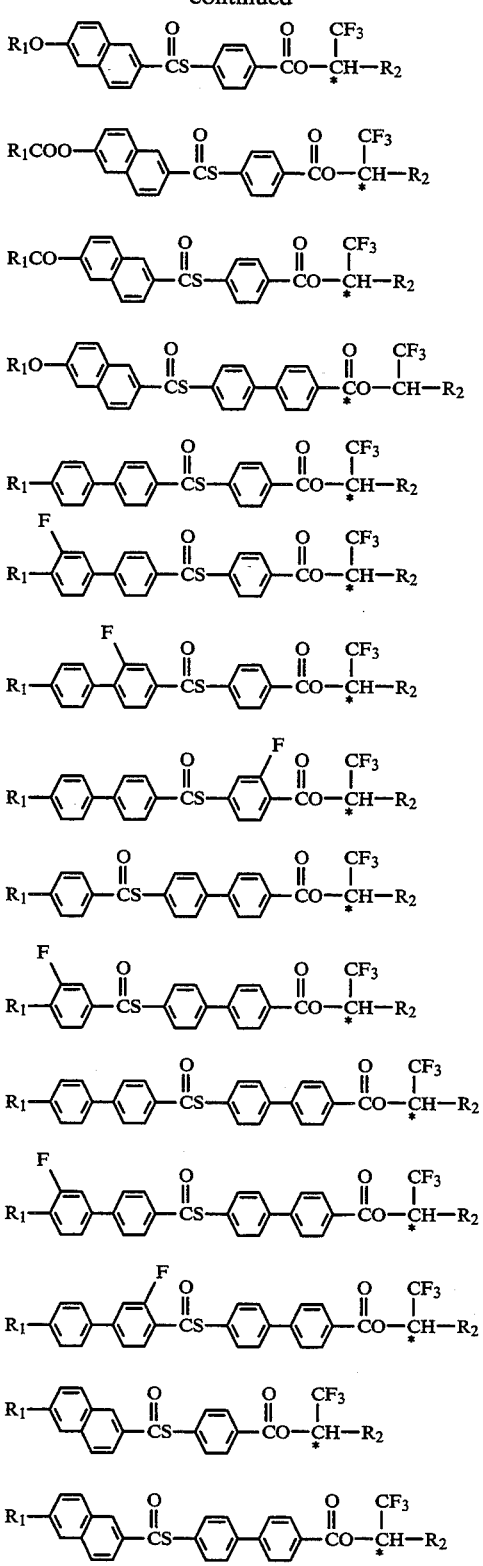

According to the present invention, a novel antiferroelectric liquid crystal compound having a thioester linkage can be provided, and the liquid crystal has a very high response speed.

EXAMPLE

The present invention will now be described in further detail with reference to Examples. However, it should be understood that the present invention is by no means restricted by such specific Examples.

EXAMPLE 1

Synthesis of 4-n-octyloxybiphenyl-4'-carboxylic acid 4-(1,1,1-trifluoro-2-octyloxycarbonyl)phenylthiol ester

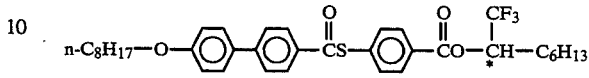

1) Synthesis of bis(4-benzoic acid) disulfide

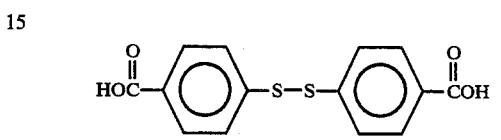

To 800 ml of ethanol containing 35 g of 4-mercaptobenzoic acid, was added 100 ml of 35% hydrogen peroxide solution, and the mixture was stirred for 8 hours at an ambient temperature. The crystals precipitated were separated by filtration, then washed with water-containing ethanol and water in this order, which were dried to obtain 28.7 g of bis(4-benzoic acid) disulfide.

2) Synthesis of bis[4-(1,1,1-trifluoro-2-octyloxycarbonyl)phenyl disulfide

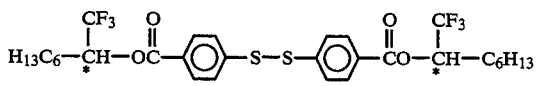

In the mixture of 200 ml of methylene chloride and 100 ml of thionyl chloride, 10 g of the compound obtained in the reaction 1) mentioned above was heated with the addition of a few drops of dimethyl formamide for 2 hours to reflux. Unaltered thionyl chloride and methylene chloride were distilled off under a reduced pressure to obtain an acid chloride.

To a solution which was prepared by dissolving 12.6 g of (R)-(+)-1,1,1-trifluoro-2-octanol [α] $D^{20}$=+25.6 (measured in $CHCl_3$ at a concentration of 0.9951% by weight), 6.9 g of triethyl amine, and a catalytic amount of dimethylamino pyridine in 100 ml of methylene chloride, was slowly added dropwise a solution which was prepared by dissolving the acid chloride mentioned above in 100 ml of methylene chloride, with stirring at a temperature of 0° C.

After the completion of the dropping, the solution was subjected to reaction for 12 hours at an ambient temperature. Then, the reaction mixture was washed with 1N hydrochloric acid and saturated salt water in this order. The solvent was distilled off under a reduced pressure, and the residues thus obtained were purified by a silica gel chromatography to obtain 18 g of bis[4-(1,1,1-trifluoro-2-octyloxycarbonyl)phenyl] disulfide.

3) Synthesis of 4-n-octyloxybiphenyl-4'-carboxylic acid 4-(1,1,1-trifluoro-2-octyloxycarbonyl)phenylthiol ester

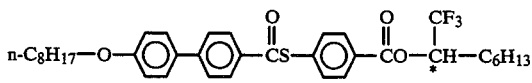

In 390 ml of acetonitrile, 9 g of the compound obtained in the reaction 2) mentioned above, 2.3 g of 4-n-octyloxybiphenyl-4'-carboxylic acid, and 1.23 g of triphenyl phosphine were heated with stirring. After cooling, the crystals precipitated were separated by filtation and then purified by a silica gel chromatography to obtain 1.8 g of 4-n-octyloxybiphenyl-4'-carboxylic acid 4-(1,1,1-trifluoro-2oxtyloxycarbonyl)phenylthiol ester.

The phase transition temperatures (°C.) observed with a microscope equipped with a hot stage were as follows:

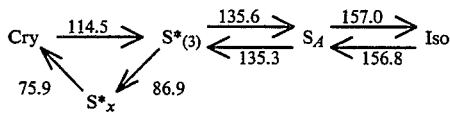

$S^*_x$ is an unknown liquid crystal phase.

EXAMPLE 2

Synthesis of 4-n-nonyloxybiphenyl-4'-carboxylic acid 4-(1,1,1-trifluoro-2-octyloxycarbonyl)phenylthiol ester

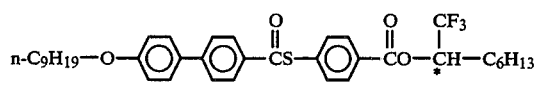

Example 1 was repeated except that 2.5 g of n-nonyloxybiphenyl-4'-carboxylic acid was used instead of n-octyloxybiphenyl-4'-carboxylic acid used in the reaction 3) in Example 1.

The phase transition temperatures (°C.) observed with a microscope equipped with a hot stage were as follows:

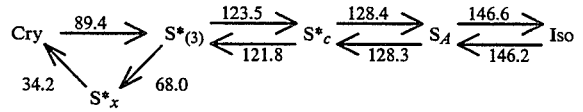

EXAMPLE 3

Synthesis of 4-n-decyloxybiphenyl-4'-carboxylic acid 4-(1,1,1-trifluoro-2-octyloxycarbonyl)phenylthiol ester

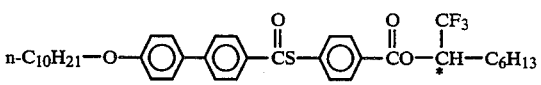

Example 1 was repeated except that 2.6 g of n-decyloxybiphenyl-4'-carboxylic acid was used instead of n-nonyloxybiphenyl-4'-carboxylic acid used in the reaction 3) in Example 1.

The phase transition temperatures (°C.) observed with a microscope equipped with a hot stage were as follows:

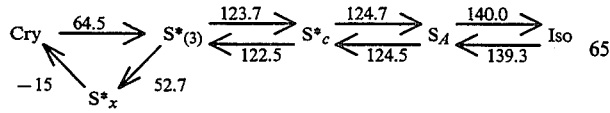

EXAMPLE 4

The liquid crystal compound obtained in Example 1 was filled in the form of an isotropic phase to a liquid crystal cell having a cell thickness of 1.9 μm and having rubbed polyimide oriented films on ITO electrode substrates to prepare a liquid crystal thin film cell.

The liquid crystal cell thus prepared was arranged on a polarizing microscope equipped with a photomultiplier where two polarizing plates were orthogonally arranged with each other, in such a state that the visual field is dark when voltage is 0 V.

The liquid crystal cell was slowly cooled down to the phase SA at a temperature gradient of 0.1° to 1.0° C./min. The cell was further cooled down and applied with a pulse voltage of ±30 V and 5 msec wide at a temperature of 95° C. From the change in light transmittance (10%–90%), a response time of 1.9 μsec was obtained.

From the result, it can be understood that the anitiferroelectric liquid crystal of the present invention shows a very high response speed.

We claim:

1. An antiferroelectric liquid crystal compound represented by the following formula:

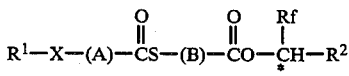

wherein $R^1$ and $R^2$ are independently selected from $C_3$–$C_{18}$ alkyl groups, respectively, Rf is a fluorinated lower alkyl group, X is selected from the group consisting of —O—, —COO—, —OCO—, —CO—, and a single bond, (A) and (B) is each independently selected from the group consisting of 1,4-phenylene, biphenylene, and naphthalene group which may be substituted with a halogen atom, and the C having an asterisk indicates an asymmetric carbon atom.

2. The antiferroelectric liquid crystal compound according to claim 1, wherein the (A) is a group selected from the group consisting of

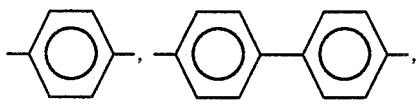

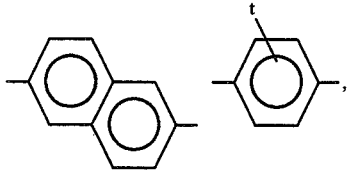

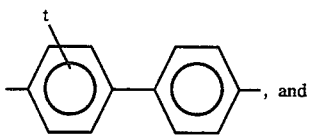, and

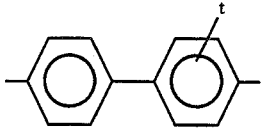

and the (B) is a group selected from the group consisting of

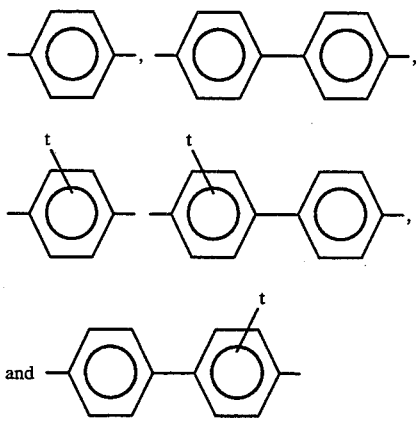

wherein t represents a halogen atom and Rf is selected from the group consisting of —CF₃, —C₂F₅, —CHF₂, and —CH₂F.

3. The antiferroelectric liquid crystal compound according to claim 2, wherein the (A) group is

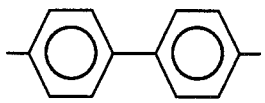

and the (B) group is

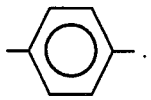

4. A process for producing an antiferroelectric liquid crystal compound comprising subjecting an acid halide represented by the following formula:

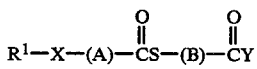

wherein $R^1$ is a $C_3$–$C_{18}$ alkyl group, X is selected from the group consisting of —O—, —COO—, —OCO—, —CO—, and a single bond, (A) and (B) is each independently selected from the group consisting of 1,4-phenylene, biphenylene, and naphthalene which may be substituted with a halogen atom, and Y represents a halogen atom, to an esterification with an optically active haloalkyl-2-alkanol represented by the following formula:

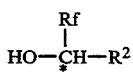

wherein $R^2$ is a $C_3$–$C_{18}$ alkyl group, and Rf is selected from the group consisting of —CF₃, —C₅, —CHF₂, and —CH₂F.

5. A process for producing an antiferroelectric liquid crystal compound comprising subjecting a disulfide diacid chloride represented by the following formula:

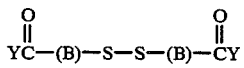

wherein (B) is selected from the group consisting of 1,4-phenylene, biphenylene, and naphthalene which may be substituted with a halogen atom, and Y represents a halogen atom, to an esterification with an optically active haloalkyl-2-alkanol or haloalkyl-3-alkanol represented by the following formula:

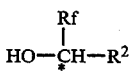

wherein $R^2$ is a $c_3$–$C_{18}$ alkyl group, and Rf is selected from the group consisting of —CF₃, —C₂F₅, —CHF₂ and —CH₂F, to obtain an ester represented by the following formula:

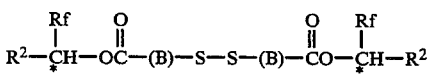

and then reacting the ester with a carboxylic acid represented by the following formula:

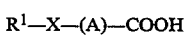

wherein $R^1$ is a $C_3$–$C_{18}$ alkyl group, X is selected from the group consisting of —O—, —COO—, —OCO—, —CO—, and a single bond, (A) is a group selected from the group consisting of 1,4-phenylene, biphenylene, and naphthalene which may be substituted with a halogen atom, or its acid halide.

6. An antiferroelectric liquid crystal compound according to claim 1, wherein Rf is selected from the group consisting of —CF₃, —C₂F₅, CHF₂, and —CH₂F, X is selected from the group consisting of —O—, —COO—, —CO—, and a single bond, the (A) group is selected from the group consisting of:

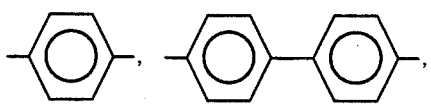

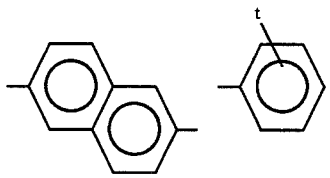

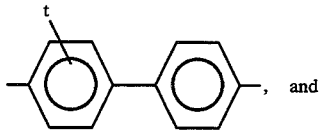

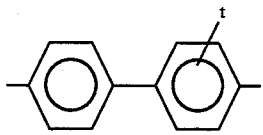

and the (B) is a group selected from the group consisting of

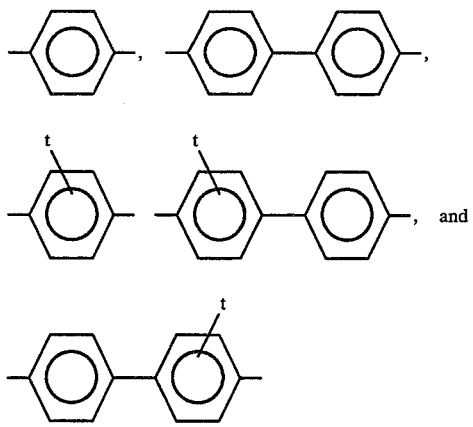

wherein t represents a halogen atom.

7. A process for producing an antiferroelectric liquid crystal compound according to claim 4 wherein X is selected from the group consisting of —O—, —OCO—, —COO—, —CO—, and a single bond, the (A) group is selected from the group consisting of

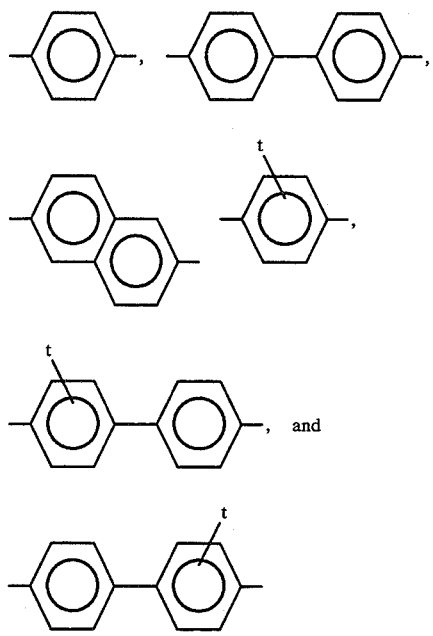

the (B) group is selected from the group consisting of

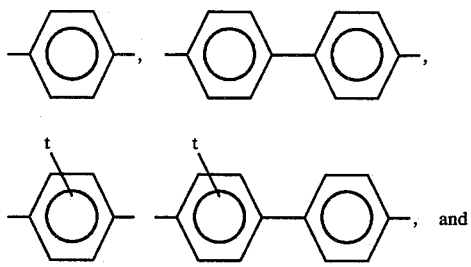

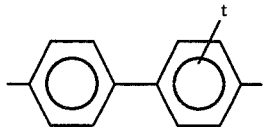

t represents a halogen atom, and Rf is selected from the group consisting of —CF$_3$—, —C$_2$F$_5$, —CHF$_2$, —CH$_2$F.

8. A process for producing an antiferroelectric liquid crystal compound according to claim 5, wherein X is selected from the group consisting of —O—, —OCO—, —COO—, —CO—, and a single bond, the (A) is selected from the group consisting of

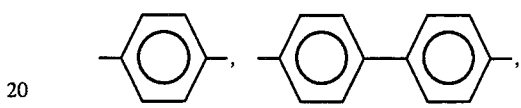

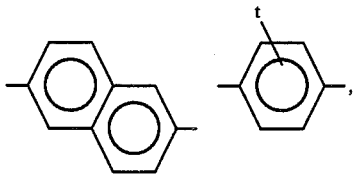

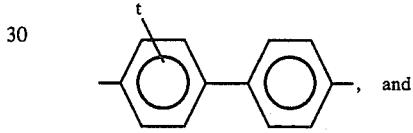

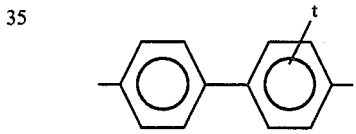

the (B) is selected from the group consisting of

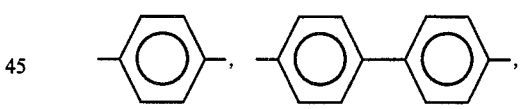

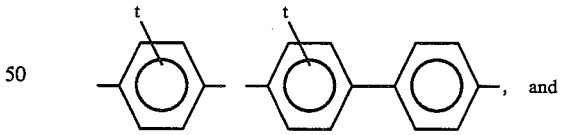

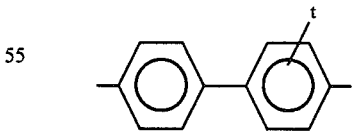

wherein t represents halogen.

9. A process for producing an antiferroelectric liquid crystal compound according to claim 7 wherein X is selected from the group consisting of —O—, —COO—, —CO—, and a single bond.

10. A process for producing an antiferroelectric liquid compound according to claim 8, wherein X is selected from the group consisting of —O—, —COO—, —CO— and a single bond.

* * * * *